United States Patent
Peng et al.

(10) Patent No.: US 8,042,414 B2
(45) Date of Patent: Oct. 25, 2011

(54) WIPE SAMPLING ASSEMBLY

(75) Inventors: Hua Peng, Beijing (CN); Jianhua Liu, Beijing (CN); Yangtian Zhang, Beijing (CN); Zhongxia Zhang, Beijing (CN); Wei Chen, Beijing (CN)

(73) Assignee: Nuctech Company Limited, Beijing (CN)

( * ) Notice: Subject to any disclaimer, the term of this patent is extended or adjusted under 35 U.S.C. 154(b) by 360 days.

(21) Appl. No.: 12/341,275

(22) Filed: Dec. 22, 2008

(65) Prior Publication Data

US 2009/0165577 A1 Jul. 2, 2009

(30) Foreign Application Priority Data

Dec. 29, 2007 (CN) .......................... 2007 1 0308542

(51) Int. Cl.
*G01N 1/04* (2006.01)
(52) U.S. Cl. .................................................. 73/864.71
(58) Field of Classification Search ............... 73/864.71, 73/864.91, 864.31
See application file for complete search history.

(56) References Cited

U.S. PATENT DOCUMENTS

| | | | |
|---|---|---|---|
| 3,074,276 A | 1/1963 | Moos | |
| 4,846,167 A | 7/1989 | Gordon et al. | 73/864.71 |
| 4,848,167 A | 7/1989 | Gordon et al. | 73/864.71 |
| 5,571,976 A | 11/1996 | Drolet | 73/864.71 |
| 5,814,522 A | 9/1998 | Zimmer et al. | 436/170 |
| 5,994,149 A | 11/1999 | Robinson et al. | 436/518 |
| 6,397,690 B1 | 6/2002 | Schroder et al. | 73/864.71 |
| 2003/0113906 A1 * | 6/2003 | Sangha et al. | 435/287.2 |

FOREIGN PATENT DOCUMENTS

| | | |
|---|---|---|
| CN | 2563564 | 7/2003 |
| CN | 201181263 | 1/2009 |
| EP | 0 750 185 A2 | 12/1996 |
| EP | 1 177 769 A2 * | 7/2001 |
| GB | 185 571 A | 7/1987 |
| GB | 2 253 337 | 9/1992 |
| JP | 2005-189123 | 7/2005 |
| WO | WO 97/38294 | 10/1997 |
| WO | WO 00/76664 | 12/2000 |
| WO | WO 2006/038023 | 4/2006 |

* cited by examiner

*Primary Examiner* — Hezron E Williams
*Assistant Examiner* — Nathaniel Kolb
(74) *Attorney, Agent, or Firm* — Westman, Champlin & Kelly, P.A.

(57) ABSTRACT

A wipe sampling assembly used for an ion mobility spectrometer is disclosed. The wipe sampling assembly comprises three layers in which the upper layer and the lower layer are protective paper sheets, while the middle layer is a sampling swab. The swab will not be contaminated when not in use as it is covered by the two protective paper sheets. The hand can only contact the protective paper and will not contact the swab while sampling to prevent the swab from being contaminated. The above wipe sampling assembly is used with no need for any additional device, thus making it easy to operate and carry.

5 Claims, 1 Drawing Sheet wiping state introducing state

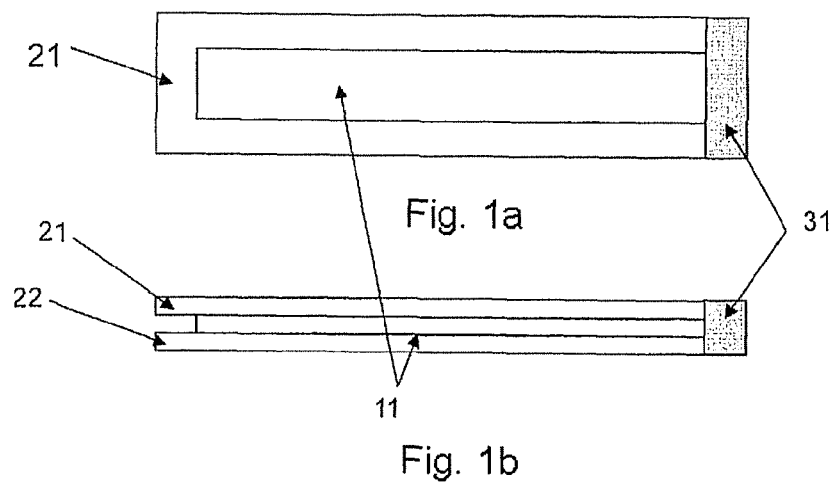
Fig. 1a
Fig. 1b
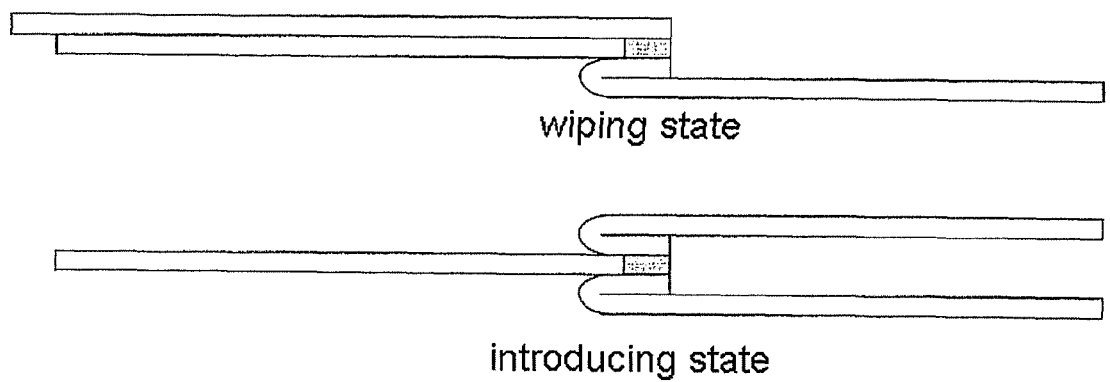
wiping state
introducing state
Fig. 2

WIPE SAMPLING ASSEMBLY

The present application claims priority of Chinese patent application Serial No. 200710308542.5, filed Dec. 29, 2007, the content of which is hereby incorporated by reference in its entirety.

BACKGROUND OF THE INVENTION

1. Field of the Invention

The present invention relates to a wipe sampling assembly used for an ion mobility spectrometer to collect particulate samples on the surface of an article.

2. Description of the Related Art

Ion mobility spectrometry is a rapid, sensitive and portable technique for field detection. The technique has been widely applied by military and security inspection agencies to detect toxic chemical agents, explosives, illicit drugs etc.

When an ion mobility spectrometer is used to detect contraband materials, a particulate sampling method is most usually employed. A swab is swiped over the surface of an article to collect any particles of explosives or drugs and the swab inserted into the inlet port of the spectrometer. The analyte is then thermally desorbed from the swipe, enter the ionization chamber and pass along the drift tube where they are detected and identified.

At present, there are mainly two types of particulate sampling modes adopted by the ion mobility spectrometer:

1. A Wipe Sampling Mode in which the Swab is Held with a Hand During Wiping and Sampling The above wipe sampling mode is performed by using a hand to hold the swab directly and swipe over a surface for sample collection. In order to prevent the hand from contacting the surface (since the contaminated hand may interfere with sample collection and detection), the swab and the corresponding inlet port has to be made large. It will not only cause a waste of swabs, but more importantly, heat can not be concentrated so that heating efficiency will be greatly reduced due to the large-sized inlet, which may adversely affect the detection sensitivity of the spectrometer. Moreover, more electrical energy is needed. Accordingly, the operating time of a battery will be shortened, thereby leading to the performance degradation of the instrument. In addition, since the swab contacts directly with the hand, dust-free gloves must be worn and frequently replaced to prevent a cross contamination between the hand and the swab so that the sampling operation is very inconvenient.

2. A Wipe Sampling Mode in which a Sampling Strip is Gripped by a Wiping Device During Wiping and Sampling The above wipe sampling mode uses smaller sampling swabs which are suitable to an ion mobility spectrometer with a small inlet port. However, since a dedicated wiping device is used, the sampling operation is still inconvenient.

SUMMARY OF THE INVENTION

In order to overcome at least some of the above problems, one objective of the present invention is to provide a wipe sampling assembly with the use of which sampling sheets can not be contaminated during sampling.

Another objective of the present invention is to provide a wipe sampling assembly in which a sampling sheet thereof may be in the form of a small thin strip suitable to an ion mobility spectrometer with a small inlet port. The wipe sampling assembly is held directly by a hand during sampling instead of using a wiping device to avoid the cross contamination between the hand and the sampling sheet and make it easy to operate and carry.

In accordance with an aspect of the present invention, there is provided a wipe sampling assembly comprising: a sampling sheet which is used for sample collection; a first protection sheet which overlaps and is connected with the sampling sheet at a first side of the sampling sheet, such that the first side of the sampling sheet is prevented from being contaminated.

As the wipe sampling assembly contains the first protection sheet, the top end of the wipe sampling assembly can be gripped directly by a hand, and sample collection can be performed by pressing the wipe sampling assembly via the first protection sheet to swipe over the surface of an article.

The first protection sheet may have a width substantially the same as that of the sampling sheet. Preferably, the first protection sheet has a width larger than that of the sampling sheet.

Preferably, the first protection sheet has a length larger than that of the sampling sheet, and the first protection sheet has a width larger than that of the sampling sheet.

One end of the first protection sheet may be aligned with and bonded to one end of the sampling sheet along the longitudinal direction of the sampling sheet by means of an adhesive agent.

The wipe sampling assembly may further comprise a second protection sheet which overlaps and is connected with the sampling sheet at a second side opposite to the first side of the sampling sheet, such that the second side of the sampling sheet is prevented from being contaminated.

The second protection sheet may have a width substantially the same as that of the sampling sheet. Preferably, the second protection sheet has a width larger than that of the sampling sheet.

Preferably, the second protection sheet has a length larger than that of the sampling sheet, and the second protection sheet has a width larger than that of the sampling sheet.

The first protection sheet has a width larger than that of a finger. The second protection sheet has a width larger than that of the finger.

The length of the first protection sheet and the length of the second protection sheet may be larger than that of the sampling sheet, and the width of the first protection sheet and the width of the second protection sheet may be larger than that of the sampling sheet. One end of the first protection sheet, one end of the second protection sheet and one end of the sampling sheet may be aligned and bonded together along the longitudinal direction of the sampling sheet by means of an adhesive agent.

At least one of the assembly components including the sampling sheet, the first protection sheet and the second protection sheet may be made of paper.

At least one of the first protection sheet and the second protection sheet may be transparent.

With the wipe sampling assembly according to the present invention, with no need for any dedicated wiping device, field sampling can be performed by using a bag of the wipe sampling assemblies which is convenient to use and carry. Thus, a simple and practical sampling means is provided for the ion mobility spectrometer.

BRIEF DESCRIPTION OF THE DRAWINGS

FIG. 1a is a top view of a wipe sampling assembly according to an embodiment of the present invention.

FIG. 1b is a side view of the wipe sampling assembly according to an embodiment of the present invention.

FIG. 2 is a schematic view of a method of using the wipe sampling assembly according to an embodiment of the present invention.

DETAILED DESCRIPTION OF THE PREFERRED EMBODIMENTS

As shown in FIGS. 1a and 1b, the wipe sampling assembly in accordance with the present invention comprises: a sampling sheet 11 which is used for sample collection; a first protection sheet 21 which overlaps and is bonded with the sampling sheet 11 at a first side (the upper side in FIG. 1b) of the sampling sheet 11, such that the first side of the sampling sheet 11 is prevented from being contaminated.

Though the wipe sampling assembly shown in FIGS. 1a and 1b comprises a first protection sheet 21 and a second protection sheet 22 on either side thereof, the invention is not limited thereto. It should be noted that a cross contamination between a hand and the sampling sheet 11 can be prevented while performing sample collection with the sampling sheet held directly by a hand if only the first protection sheet 21 is provided and the second protection sheet 22 can be omitted.

The first protection sheet 21 has a width substantially the same as that of the sampling sheet 11. In this case, though the hand may contact the surface of the article, the cross contamination between the hand and the sampling sheet can be prevented.

According to an embodiment of the present invention, the first protection sheet 21 has a width larger than that of the sampling sheet 11.

Preferably, the first protection sheet 21 has a length larger than that of the sampling sheet 11, and the first protection sheet 21 has a width larger than that of the sampling sheet 11.

According to one embodiment of the present invention, one end of the first protection sheet 11 is aligned with and bonded to one end of the sampling sheet 11 along the longitudinal direction of the sampling sheet 11 by means of an adhesive agent. As shown in FIGS. 1a and 1b, one end of the first protection sheet 21 is bonded with one end of the sampling sheet 11 at a joint 31. Obviously, the first protection sheet 21 may be bonded with the sampling sheet 11 at any other position, for example, the middle portion of the sampling sheet 11, as long as the cross contamination between the hand and the sampling sheet 11 can be prevented. If the first protection sheet 21 is bonded with the sampling sheet 11 at the middle portion of the sampling sheet 11, the cross contamination between the hand and the sampling sheet may also be prevented when the sampling sheet is held by the hand to perform swipe sampling on the surface of an article. However, the first protection sheet 21 needs to be separated from the middle portion of the sampling sheet 11 after swipe sampling.

For example, a silicone rubber adhesive may be used as the adhesive agent.

Moreover, in addition to the adhesive-bonded connecting manner, the first protection sheet 21 may be bonded with the sampling sheet 11 by adopting various other modes suitable for this application. For example, two incisions are provided side by side at one end of the first protection sheet 21, and a projection narrower than the sampling sheet 11 is provided at an end of the sampling sheet 11; when the projection is inserted into the two incisions, the first protection sheet 21 and the sampling sheet 11 will be connected together.

As shown in FIGS. 1a and 1b, the wipe sampling assembly further comprises the second protection sheet 22 which overlaps and is bonded with the sampling sheet 11 at a second side of the sampling sheet 11, such that the second side of the sampling sheet 11 (a lower side in FIG. 1b) opposite to its first side is prevented from being contaminated.

Similar to the first protection sheet 21, the second protection sheet 22 has a width substantially the same as that of the sampling sheet 11. Preferably, the second protection sheet 22 has a width larger than that of the sampling sheet 11. According to one embodiment of the present invention, the second protection sheet 22 has a length larger than that of the sampling sheet 11, and the second protection sheet 22 has a width larger than that of the sampling sheet 11.

In order to prevent the finger from contacting the surface of an article, the first protection sheet may have a width substantially larger than that of the finger. Also, the second protection sheet may have a width substantially larger than that of the finger.

According to one embodiment of the present invention, the length of the first protection sheet 21 and the length of the second protection sheet 22 are larger than that of the sampling sheet 11; the width of the first protection sheet 21 and the width of the second protection sheet 22 are larger than that of the sampling sheet 11; one end of the first protection sheet 21, one end of the second protection sheet 22 and one end of the sampling sheet 11 are aligned and connected together along the longitudinal direction of the sampling sheet by means of an adhesive agent (such as a silicone rubber adhesive). As shown in FIGS. 1a and 1b, one end of the first protection sheet 21, one end of the second protection sheet 22 and the one end of the sampling sheet 11 are bonded together at joint 31 by means of an adhesive agent.

There are other alternatives of the mode to bond one end of the first protection sheet 21, one end of the second protection sheet 22 and one end of the sampling sheet together. The three ends may also be folded together (for example, be folded one time or more times), and then be bound or stamped together like a book. In addition, one end of the first protection sheet 21, one end of the second protection sheet 22 and one end of the sampling sheet 11 may be clamped together with a clamp. The wipe sampling assembly only comprising only the first protection sheet 21 and the sampling sheet 11 may be bonded in a similar manner as above.

According to one embodiment of the present invention, at least one of the first protection sheet 21, the second protection sheet 22 and the sampling sheet 11 may be made of a material selected from a group consisting of paper, plastic film, plastic cloth, tin foil or the combination thereof.

According to one embodiment of the present invention, the sampling swab is cut into a paper scrip having a length of 6 cm and a width of 1 cm; the protection sheet is cut into a paper scrip (made of clean and interferent-free material) having a length of 7 cm and a width of 2 cm. Preferably, the paper should be clean and have no interfering impurity. The sampling swab (used as the sampling sheet 11) is placed between two paper scrips for protection (used as the first protection sheet 21 and the second protection sheet 22). With one end aligned, the three layers of paper scrips are glued at the aligned end.

As for the above wipe sampling assembly, in the case that the widths of the two protection paper sheets are larger than that of the sampling sheet as well as that of the finger, and the lengths of the two protection paper sheets are larger than that of the sampling sheet, the sampling sheet is covered by the protection paper sheets and will not be contaminated when not in use; moreover, the hand will only contact the protection paper sheets, instead of the sampling sheet and the article to be swiped when in use, thus the sampling sheet and the hand will also not be contaminated.

A method of using the wipe sampling assembly according to the present invention will be illustrated by referring to FIG. 2 in the following paragraph. When the assembly is used, a layer of the protection paper (used as the second protection sheet 22) is tucked up backward so as to expose the swab (used as the sampling sheet 11). Then with the swab facing towards the surface of an article to be swiped, use the first finger or the middle finger to press on another layer of protection paper (used as the first protection sheet 21) to perform wipe sampling over the surface of the article. After the sampling operation is completed, the layer of protection paper (the one being pressed during sampling) is tucked up backwards to draw together with the other layer of protection paper, and the two layers of protection paper are held with a hand to introduce the swab into the inlet port of an ion mobility spectrometer for detection and identification.

Obviously, when only the first protection sheet 21 is used and the second protection sheet 22 is omitted, the above step described as "a layer of protection paper is tucked up backwards so as to expose a swab" may be omitted.

In addition, though the sampling sheet 11 in figures is rectangular, it may be a strip in any suitable shapes. Moreover, though appearing rectangular, the first protection sheet 21 and the second protection sheet 22 may be designed to be in a variety of other shapes such as square, round, elliptical, triangular and the like as long as they still have the function to prevent the cross contamination between the hand and the sampling swab while swiping over the surface of an article.

What is claimed is:

1. A wipe sampling assembly, comprising:
    a sampling sheet which is used for sampling;
    a first protection sheet which overlaps and is bonded with the sampling sheet at a first side of the sampling sheet, such that the first side of the sampling sheet is prevented from being contaminated; and
    a second protection sheet which overlaps and is bonded with the sampling sheet at a second side of the sampling sheet, such that the second side opposite to the first side of the sampling sheet is prevented from being contaminated;
    wherein the length of the first protection sheet and the length of the second protection sheet is larger than that of the sampling sheet, and the width of the first protection sheet and the width of the second protection sheet is larger than that of the sampling sheet; and
    wherein one end of the first protection sheet, one end of the second protection sheet and one end of the sampling sheet are aligned and connected together along the shorter dimension of the sampling sheet.

2. The wipe sampling assembly according to claim 1, wherein:
    the one end of the first protection sheet, the one end of the second protection sheet and the one end of the sampling sheet are connected together by means of an adhesive agent.

3. The wipe sampling assembly according to claim 1, wherein:
    at-least one of the first protection sheet, the second protection sheet and the sampling sheet is made of paper.

4. The wipe sampling assembly according to claim 1, wherein:
    the first and second protection sheets have a width substantially larger than that of a finger.

5. The wipe sampling assembly according to claim 1, wherein:
    at least one of the first protection sheet and the second protection sheet is transparent.

* * * * *